US00PP29864P2

(12) United States Plant Patent
Verschoor

(10) Patent No.: US PP29,864 P2
(45) Date of Patent: Nov. 20, 2018

(54) ***PHLOX* PLANT NAMED 'VERSPURPLE'**

(50) Latin Name: *Phlox paniculata*
Varietal Denomination: Verspurple

(71) Applicant: Adrianus Verschoor, Haarlem (NL)

(72) Inventor: Adrianus Verschoor, Haarlem (NL)

( * ) Notice: Subject to any disclaimer, the term of this patent is extended or adjusted under 35 U.S.C. 154(b) by 0 days.

(21) Appl. No.: 15/731,195

(22) Filed: May 1, 2017

(51) Int. Cl.
*A01H 5/02* (2018.01)

(52) U.S. Cl.
USPC ..... Plt./320

(58) Field of Classification Search
USPC ..... Plt./263.1, 320
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Phlox* plant named 'Verspurple', characterized by its broadly upright and relatively compact plant habit; freely flowering habit; large inflorescences with purple violet-colored flowers; long flowering period; good garden performance; and relative tolerance to Powdery Mildew.

2 Drawing Sheets

Botanical designation: *Phlox paniculata.*
Cultivar denomination: 'VERSPURPLE'.

BACKGROUND OF THE INVENTION

The present invention relates to a new and distinct cultivar of *Phlox* plant, botanically known as *Phlox paniculata* and hereinafter referred to by the name 'Verspurple'.

The new *Phlox* plant is a product of a planned breeding program conducted by the Inventor in Haarlem, The Netherlands. The objective of the breeding program was to create new compact and freely-flowering *Phlox* plants with attractive flower colors.

The new *Phlox* plant originated from an open-pollination in Haarlem, The Netherlands, of an unnamed selection of *Phlox paniculata* as the female, or seed, parent, not patented with an unknown selection of *Phlox paniculata* as the male, or pollen, parent. The new *Phlox* plant was discovered and selected by the Inventor as a single flowering plant from within the progeny of the stated open-pollination in a controlled environment in Haarlem, The Netherlands during the summer of 2013.

Asexual reproduction of the new *Phlox* plant by vegetative stem cuttings in a controlled environment in Haarlem, The Netherlands since August, 2013 has shown that the unique features of this new *Phlox* plant are stable and reproduced true to type in successive generations.

SUMMARY OF THE INVENTION

Plants of the new *Phlox* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Verspurple'. These characteristics in combination distinguish 'Verspurple' as a new and distinct *Phlox* plant:

1. Broadly upright and relatively compact plant habit.
2. Freely flowering habit.
3. Large inflorescences with purple violet-colored flowers.
4. Long flowering period.
5. Good garden performance.
6. Relative tolerance to Powdery Mildew.

Plants of the new *Phlox* and the female parent selection differ primarily in the following characteristics:

1. Plants of the new *Phlox* are shorter and more compact than plants of the female parent selection.
2. Flowers of plants of the new *Phlox* are more intense purple violet in color than flowers of plants of the female parent selection.
3. Plants of the new *Phlox* are healthier, stronger and more tolerant to Powdery Mildew than plants of the female parent selection.

Plants of the new *Phlox* can be compared to plants of *Phlox paniculata* 'Nicky', not patented. In side-by-side comparisons, plants of the new *Phlox* and 'Nicky' differ in the following characteristics:

1. Plants of the new *Phlox* are shorter and more compact than plants of 'Nicky'.
2. Plants of the new *Phlox* grow faster than plants of 'Nicky'.
3. Plants of the new *Phlox* are healthier, stronger and more tolerant to Powdery Mildew than plants of 'Nicky'.
4. Plants of the new *Phlox* and 'Nicky' differ in flower color as plants of 'Nicky' have blue purple-colored flowers.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet comprises a side perspective view of a typical flowering plant of 'Verspurple' grown in a container.

The photograph on the second sheet is a close-up view of a typical flowering plant of 'Verspurple'.

DETAILED BOTANICAL DESCRIPTION

The aforementioned photographs and following observations, measurements and values describe plants grown during the summer and early autumn in 17-cm containers and ground beds in an outdoor nursery in Haarlem, The Netherlands and under cultural practices typical of commercial *Phlox* production. During the production of the plants, day temperatures ranged from 14° C. to 30° C. and night temperatures ranged from 6° C. to 18° C. Plants were one year old when the photographs and description were taken. In the following description, color references are made to The Royal Horticultural Society Colour Chart, 2015 Edition, except where general terms of ordinary dictionary significance are used.

Botanical classification: *Phlox paniculata* 'Verspurple'.

Parentage:

*Female, or seed, parent*.—Unnamed selection of *Phlox paniculata*, not patented.

*Male, or pollen, parent*.—Unknown selection of *Phlox paniculata*, not patented.

Propagation:

*Type*.—By vegetative stem cuttings.

*Time to initiate roots, summer*.—About three weeks at temperatures about 20° C.

*Time to produce a rooted plant, summer*.—About six weeks at temperatures about 20° C.

*Root description*.—Fine, fibrous.

*Rooting habit*.—Freely branching; medium density.

Plant description:

*Plant and growth habit*.—Herbaceous perennial; broadly upright and relatively compact plant habit; overall shape, broad inverted triangle; moderately vigorous and moderate growth rate.

*Plant height, soil level to top of foliar plane*.—About 38.8 cm.

*Plant height, soil level to top of floral plane*.—About 52.5 cm.

*Plant width* (*spread*).—About 46.6 cm.

*Lateral branches*.—Length: About 34 cm. Diameter: About 5 mm. Internode length: About 2.7 cm. Strength: Strong. Aspect: Upright to about 30° from vertical. Texture: Smooth, glabrous. Luster: Slightly glossy. Color, developing: Close to 144A. Color, developed: Close to 144A.

Leaf description:

*Arrangement*.—Opposite, simple.

*Length*.—About 12.1 cm.

*Width*.—About 3.5 cm.

*Shape*.—Narrowly elliptic.

*Apex*.—Narrowly acute.

*Base*.—Truncate.

*Margin*.—Entire; very finely serrate, inconspicious; slightly revolute.

*Texture, upper and lower surfaces*.—Smooth, glabrous; slightly rugose.

*Luster, upper and lower surfaces*.—Slightly glossy.

*Venation pattern*.—Pinnate.

*Color*.—Developing leaves, upper surface: Close to 143A tinged with close to 203A. Developing leaves, lower surface: Close to 147B. Fully expanded leaves, upper surface: Close to 137A; venation, close to 144B. Fully expanded leaves, lower surface: Close to between 143A and 147B; venation, close to 144B.

*Petioles*.—Length: About 4 mm. Diameter: About 3 mm. Strength: Strong. Texture, upper and lower surfaces: Smooth, glabrous. Luster, upper and lower surfaces: Matte. Color, upper and lower surfaces: Close to 144B.

Flower description:

*Flower type and flowering habit*.—Single rotate and salverform flowers arranged in compound terminal panicles; flowers face upright to outwardly; panicles roughly pyramidal in shape; freely flowering habit with about 150 flowers developing per inflorescence.

*Fragrance*.—Moderately fragrant; sweet, pleasant.

*Natural flowering season*.—Plants begin flowering about eight months after planting; long flowering period, plants flower continuously from late spring throughout the summer in The Netherlands.

*Flower longevity*.—Flowers last about ten days on the plant; flowers not persistent.

*Flower buds*.—Height: About 2.3 cm. Diameter: About 5 mm. Shape: Oblanceolate. Texture: Smooth, glabrous. Luster: Matte. Color: Close to 83B to 83C; immature tube, lighter than N77B; immature calyx, close to 145D strongly tinged with close to N77C and 165A.

*Inflorescence height*.—About 15.1 cm.

*Inflorescence diameter*.—About 13.8 cm.

*Flower diameter*.—About 3.5 cm.

*Flower depth*.—About 2.6 cm.

*Throat diameter*.—About 5 mm.

*Tube length*.—About 2.2 cm.

*Tube diameter*.—About 4 mm.

*Petals*.—Quantity per flower: Typically five in a single whorl; lower 60% of petal length fused into a narrow tube; free parts slightly to moderately imbricate. Length: About 3.7 cm; lower 2.2 cm fused. Lobe width: About 2.2 cm. Shape: Free part, spatulate. Apex: Obtuse. Margin: Entire. Texture, upper surface: Smooth, glabrous; velvety. Texture, lower surface: Smooth, glabrous; slightly velvety. Texture, throat: Smooth, glabrous. Texture, tube: Moderately pubescent. Luster, upper and lower surfaces: Matte. Color: When opening, upper surface: Slightly darker and more intense than N81A. When opening, lower surface: Close to 86D. Fully opened, upper surface: Close to N81A; color becoming closer to N81A to N81B with development. Fully opened, lower surface: Close to 86D; color does not change with development. Throat: Close to N78A. Tube: Close to 77A.

*Sepals*.—Quantity per flower: Typically five in a single whorl, lower 30% of sepal length fused into a narrow tube; calyx, campanulate. Length: About 9 mm. Width: About 2 mm. Shape: Narrowly lanceolate. Apex: Narrowly apiculate. Margin: Entire. Texture, upper and lower surfaces: Smooth, glabrous. Luster, upper and lower surfaces: Matte. Color: When opening, upper surface: Close to 145A; towards the margins, close to N77C. When opening, lower surface: Close to 145D; strongly tinged with close to 165A; towards the margins, close to N77C. Fully opened, upper surface: Close to 145A; towards the margins, close to N77C. Fully opened, lower surface: Close to 145B; strongly tinged with close to 200A; towards the margins, close to N77C.

*Peduncles*.—Length: About 11.8 cm. Diameter: About 2.5 mm. Aspect: Erect. Strength: Strong. Texture: Smooth, glabrous. Luster: Slightly glossy. Color: Close to 144B to 144C.

*Pedicels*.—Length: About 6 mm. Diameter: About 0.8 mm. Angle: About 60° from the peduncle axis. Strength: Moderately strong. Texture: Moderately pubescent. Luster: Matte. Color: Close to 146A.

*Reproductive organs*.—Stamens: Quantity per flower: Typically five. Filament length: About 1 mm. Filament color: Close to N155B. Anther length: About 2 mm. Anther shape: Oblong; basifixed. Anther color: Close to 158B. Pollen amount: Moderate. Pollen color: Close to 158D. Pistils: Quantity per flower: One. Pistil length: About 1.9 cm. Stigma shape: Cleft, three-parted. Stigma color: Close to 150D. Style length: About 1.8 cm. Style color: Close to N77C. Ovary color: Close to 143A.

*Seeds and fruits*.—Seed and fruit development have not been observed on plants of the new *Phlox* to date.

Garden performance: Plants of the new *Phlox* have been observed to have good garden performance and tolerate rain, wind, high temperatures about 35° C. and to be winter hardy to USDA Hardiness Zone 6.

Disease & pest resistance: Plants of the new *Phlox* have been observed to be relatively tolerant to Powdery Mildew (*Erysiphe cichoracearum*); plants of the new *Phlox* have not been observed to be resistant to pests and other pathogens common to *Phlox* plants.

It is claimed:

1. A new and distinct *Phlox* plant named 'Verspurple' as illustrated and described.

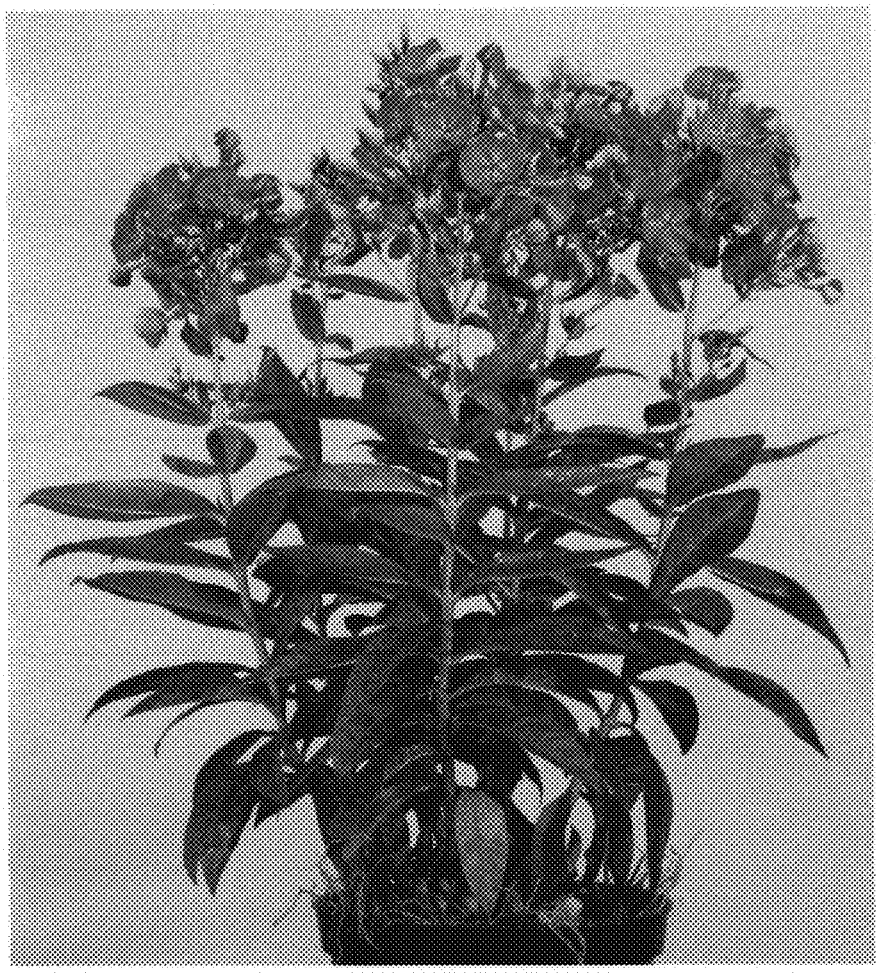

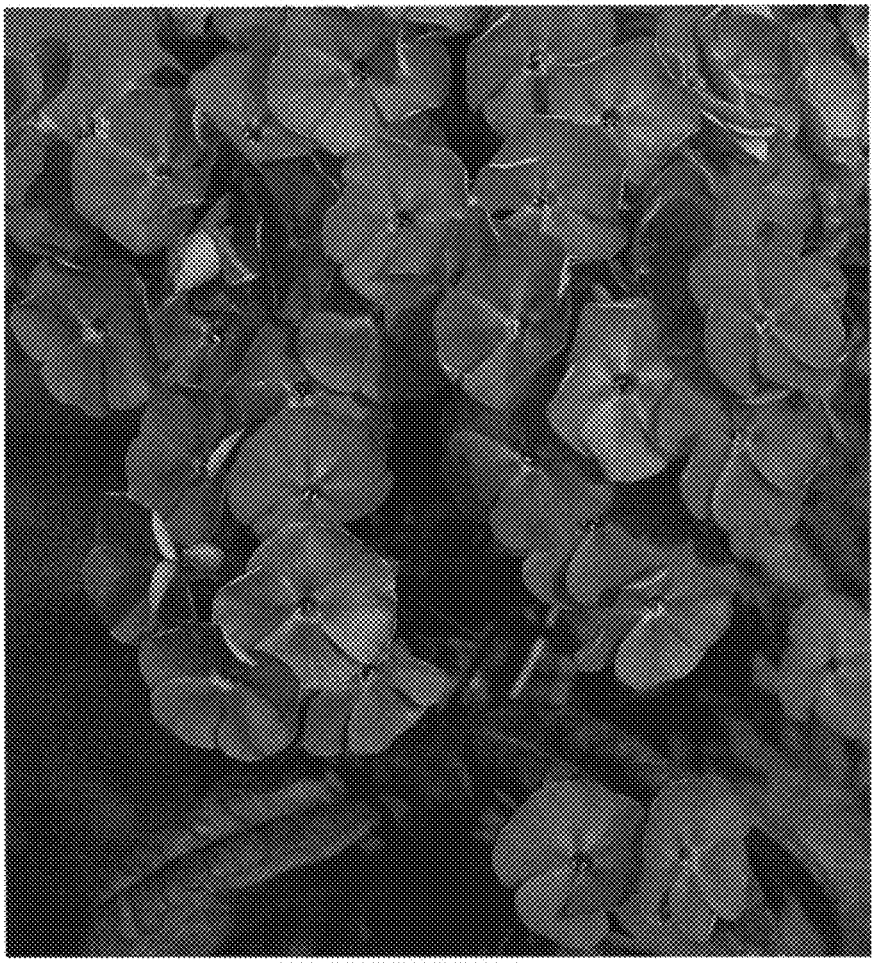

* * * * *